United States Patent [19]

Leclerc

[11] 4,327,375
[45] Apr. 27, 1982

[54] PROCESS AND APPARATUS FOR PROVIDING DATA INDICATIVE OF THE SHAPE OF LEAF-LIKE ARTICLE

[75] Inventor: Jean F. Leclerc, Orleans, France

[73] Assignee: Service d'Exploitation Industrielle des Tabacs et des Allumettes, Paris, France

[21] Appl. No.: 136,775

[22] Filed: Apr. 3, 1980

[30] Foreign Application Priority Data

Apr. 11, 1979 [FR] France .................. 79 09126

[51] Int. Cl.³ .............................................. H04N 7/18
[52] U.S. Cl. ...................................... 358/107; 358/106; 356/237
[58] Field of Search .......................... 358/105, 106, 107; 356/237, 239; 364/515, 516, 517

[56] References Cited

U.S. PATENT DOCUMENTS 4,079,416  3/1978  Faami et al. ........................ 358/107

Primary Examiner—John C. Martin
Assistant Examiner—Edward L. Coles
Attorney, Agent, or Firm—Holman & Stern

[57] ABSTRACT

Process and apparatus for providing digital data indicative of the contour of a leaf-like article, e.g. a tobacco leaf, and the flaws (holes) that it may comprise, from a video signal composed of image lines. The video signal is coded by comparing same with thresholds so as to detect transitions. The number n of points pertaining to a hole is compared with a threshold $n_1$, firstly within a line X, then in successive lines X, X+1, and the code is converted to "flaw" when $n \geq n_1$. Only when they precede a transition, the coded signals are stored in a memory in the order of appearance of the lines. The stored signals are readout in the opposite order, whereby all the codes pertaining to a given flaw can be rendered uniform and the codes pertaining to unsignificant flaws can be suppressed.

7 Claims, 8 Drawing Figures

PROCESS AND APPARATUS FOR PROVIDING DATA INDICATIVE OF THE SHAPE OF LEAF-LIKE ARTICLE

BACKGROUND OF THE INVENTION

The present invention relates to a process and apparatus for providing in digital form information indicative of the outer contour of a leaf-like article and the holes that it may comprise, when these holes must be taken into consideration, in view of their dimensions, for the use of the product, from an analog video signal composed of image lines and representing the image of said article placed on a support.

When pieces of determined shape have to be cut from a leaf-like article whose outer shape is variable and which may comprise holes, for example when cigar wrappers are cut out from a tobacco leaf, every effort must be made to obtain an optimum use of the product, and processes for automatic calculation have been developed to this end.

The basic information that the computer must receive is the outer contour of the product and the holes that it may comprise, insofar as these holes are of such dimensions that they must be taken into account to determine the optimum cut-out pattern.

However, the analog video signal cannot be processed by the computer and it must firstly be converted into a digital signal, according to the known process which consists in comparing the video signal, for each image dot, with a determined threshold, and in coding the dot "1" or "0" according to whether the intensity of the signal is greater than or less than the threshold. The threshold will be suitably chosen so that the signal is coded "1" (or "0") for the support and "0" (or "1") for the article.

However, the digital signal thus obtained represents an extremely large amount of information, and the processing of such a signal necessitates memories of very large capacity and, more generally, very heavy equipment, if it is desired that the duration of the processing is compatible with practical requirements. A considerable compression of this signal is therefore indispensable.

In addition, the holes are to be taken into consideration only from a certain dimension, corresponding to a number $n_1$ of image dots, which implies that the corresponding criterion is applied to the signal. A specific processing is necessary to this end.

In short, the problem raised consists in transmitting to the computer information in digital form containing all the necessary data, while being of minimum volume.

SUMMARY OF THE INVENTION

The process according to the invention comprises, to this end, the following steps:

The transitions in the digital signal thus obtained are detected; this digital signal is coded as a "leaf" signal or word when the signal is a "0" (resp. "1") and as a "support" word when the signal is "1" (resp. "0") and when it relates to a hole; the number n of dots coded "1" (or "0") which follow, firstly in a line X (direction Y), then in consecutive lines X, X+1, etc. (direction X) is compared with the above-mentioned threshold, expressed by a number $n_1$ of image dots; the "support" signals are converted, if $n \geq n_1$, into "flaw" signals, and they are transmitted unchanged if $n < n_1$; only the signals preceding a transition, accompanied by the corresponding position data Y, are stored, by writing them in the order of appearance of the lines; the stored information is read in the order opposite the order of writing whereby a line X+1 is read before line X; the signals other than the "support" signals are transmitted unaltered, and the "support" signals are processed in the following manner; if a "support" signal of a line X is located in the vicinity of a "flaw" signal present in line X+1 read previously, it is converted into a "flaw" signal, otherwise, it is not transmitted.

The signals obtained by the process according to the invention represent an extremely reduced volume of information with respect to the starting video signal, and even with respect to the digital signal obtained by comparing the video signal with a threshold, as only the transitions are transmitted. In addition, only the interesting transitions are transmitted, as the processing according to the invention has suppressed those which correspond to unsignificant flaws. The resultant signal therefore contains all the necessary information, in an extremely condensed form.

BRIEF DESCRIPTION OF THE DRAWINGS

The invention will be more readily understood on reading the following description with reference to the accompanying drawings, in which.

DESCRIPTION OF THE PREFERRED EMBODIMENT

The application envisaged by the present specification concerns the analysis of the shape—outer contour, ribs and flaws—of a tobacco leaf from which cigar wrappers are to be cut out, and a computer must be supplied with the necessary data for it to elaborate a cut-out pattern ensuring an optimum use of the product.

Figure 1:
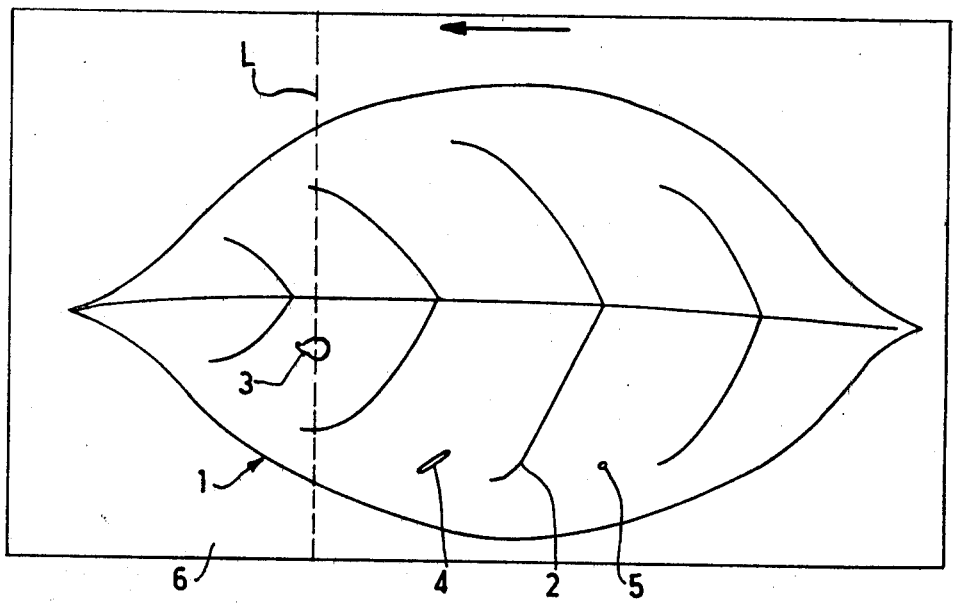
FIG. 1 shows a tobacco leaf whose shape is to be analysed.

Referring now to the drawings, FIG. 1 shows a tobacco leaf generally designated by reference 1. The data which must be available for elaborating a cigar wrapper cut-out pattern are as follows:

the outer contour of the leaf;
the shape of the ribs 2;
the contour and nature of the flaws whose dimensions are such that they must be taken into account: a distinction must here be made between a hole such as 3, which is quite undesirable in a wrapper, and a narrower slit such as 4 whose presence in a wrapper is admissible outside the edges.

On the other hand, the flaws of small dimensions such as 5 should not be taken into account as a cigar wrapper may comprise such flaws.

To analyse the shape of the leaf, a pick-up tube of the line scan type is used, and the leaf is fed in the direction of the arrow on a belt 6, the feed of the leaf thus providing the image scanning. The line scanning is effected perpendicularly to the displacement of the leaf, as shown by dashed line L.

The belt 6 constitutes a background of high luminosity, which is formed for example by a translucent material, illuminated in transparency, so as to provide a good contrast.

Figure 2A:
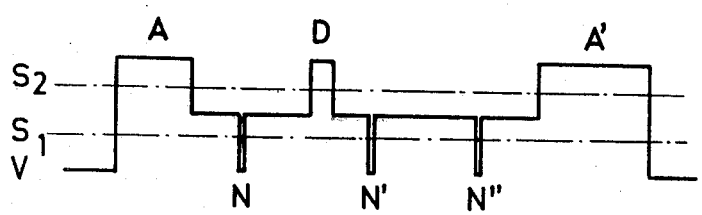
FIG. 2a represents a line of the video signal corresponding to the line indicated in FIG. 1.

FIG. 2a represents the video signal provided by the pick-up tube for line L. This signal presents three possible levels of intensity, a high level corresponding to the support (sections A and A′) and to the flaw 3 (section D), an average level corresponding to the leaf, which is sparingly opaque, and a low level corresponding to the ribs (sections N, N′, N″).

The video signal of FIG. 2a has been shown in continuous form, but it is in fact sampled and comprises 1728 image dots per line.

This signal of course is not apt to be used as such by a computer, and it must firstly be converted into a digital signal.

This conversion is effected by comparing the video signal with two fixed thresholds $S_1$ and $S_2$ so as to allow a discrimination between the three levels of the signal. The upper threshold $S_2$ is located between the average level and the high level, and the lower threshold $S_1$ is located between the low level and the medium level.

By these comparisons, two digital signals $C_1$ and $C_2$ are obtained. The signal $C_1$ represented in FIG. 2b results from the comparison with the lower threshold $S_1$, and presents logic states "0" corresponding to the ribs, whilst the signal $C_2$, shown in FIG. 2c, results from the comparison with the upper threshold $S_2$ and presents sections in logic state "1" corresponding either to the outside of the leaf, or to the flaw 3.

The digital signals thus obtained are then processed, the principle of which will be set forth with reference to the block diagram of FIG. 3. The circuits used for effecting this processing will then be described in greater detail with reference to FIGS. 5 and 6.

Figure 3:
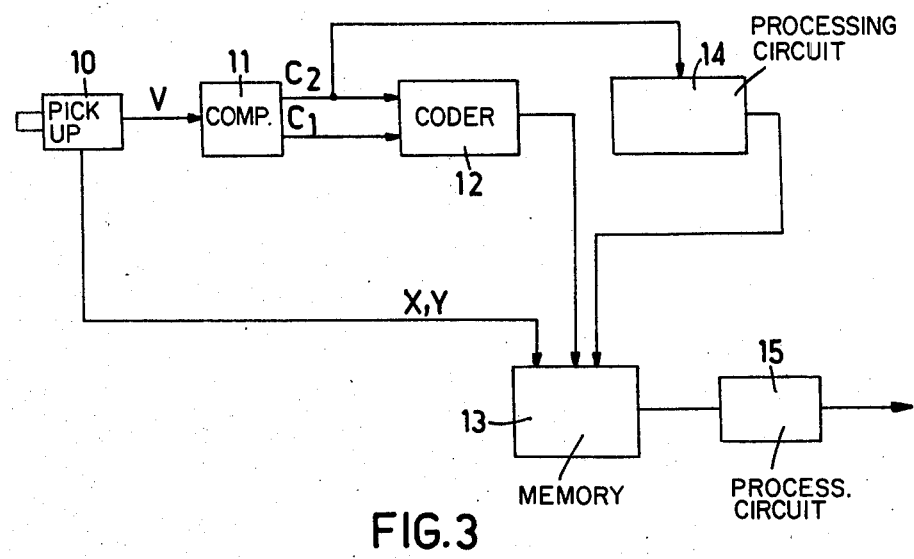
FIG. 3 is a block diagram of the device for carrying out the process according to the invention.

The diagram of FIG. 3 shows the pick-up tube 10 which furnishes the video signal V to the comparison device 11, which delivers the digital signals $C_1$ and $C_2$.

The signals $C_1$ and $C_2$ are applied to a coder 12 which causes a digital signal of 3 bits $b_0 b_1 b_2$ to correspond to each image dot and also delivers a pulse each time a transition from one state to the other occurs in at least one of the signals $C_1$ and $C_2$.

The coder 12 delivers a "rib" signal if $C_1=0$ and $C_2=0$, a "leaf" signal if $C_1=1$ and $C_2=0$ and a "support" signal if $C_1=1$ and $C_2=1$, each of these signals corresponding to a different code $b_0 b_1 b_2$.

In addition, the point immediately preceding the first support-leaf transition of a line, which corresponds to the edge of the leaf, is coded in a specific manner ("edge") instead of being coded "support".

Similarly, a specific code "end of line" has been provided for the last dot of a line, which should normally have been coded "support".

All the signals are entered in a memory 13 under the control of the "transition" pulses produced by the coder 12. This implies that if, for each dot of a line, the coder 12 delivers a code $b_0 b_1 b_2$ corresponding to the values of $C_1$ and $C_2$, only those of the signals which immediately precede a transition will be entered in the memory. At the same time as one of these signals, the position data Y of the signal in question in the line or the position data X of the line at the beginning of a line is entered, this position data being furnished by clocks associated with the pick-up tube 10.

All the signals other than "support" signals are transmitted directly from the coder 12 to the memory. The "support" signals preceding a transition, which correspond to the last dot of a flaw, are subjected to a differentiation processing according to the nature of the flaw to which they correspond.

Two criteria of differentiation are applied.

The dimension of the flaw is firstly examined along X or Y. If one of the dimensions is greater than a number $n_1$ of image dots (representing 3 millimeters in the present example), the flaw is taken into consideration. Otherwise, the flaw is considered as unsignificant (for example reference numeral 5 in FIG. 1). With a distance between dots of 0.25 mm, $n_1 = 3$ mm/0.25 mm $= 12$.

The surface of the flaw is then examined. If it is greater than a value $n_2$, the flaw is a hole, for example 3 in FIG. 1 and if it is smaller than $n_2$, it is a slit (for example 4 in FIG. 1). In the present example, $n_2$ represents 4 mm$^2$ and is therefore worth 4 mm$^2$/0.25 mm $\times$ 0.25 mm $= 64$.

This processing is effected in a circuit 14 which, in accordance with the signals $C_2$ which it receives from the comparison device 11, converts the "support" signals (S) into "slit" signals (F), "hole" signals (T), or passes the "support" signals without modifying them.

Figure 4:
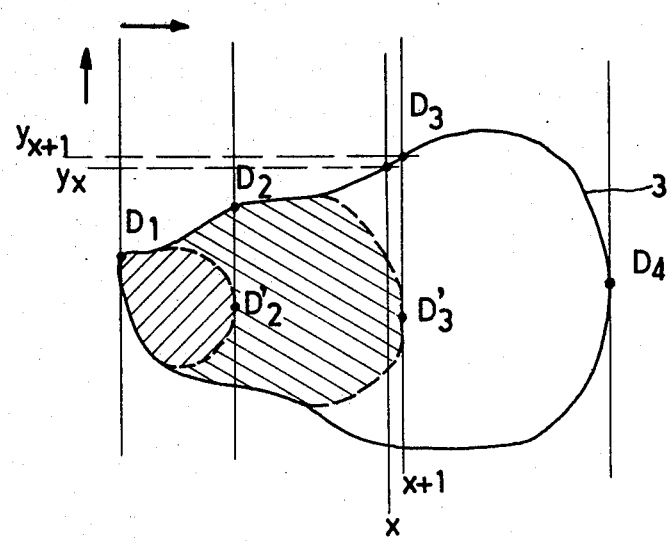
FIG. 4 is a view on a large scale of a flaw of the leaf of FIG. 1.

It should be emphasized that the application of the above criteria of differentiation is effected progressively dot by dot on each line, then line by line. This results in that the signals S from the coder 12 relative to one and the same flaw, for example to a hole, will not be converted in the same manner. This is illustrated in FIG. 4 which shows the flaw 3 of FIG. 1 on a larger scale.

The direction of analysis is indicated by the arrows. The signals preceding the transitions $D_1D_2D_3D_4$ will therefore be coded "support" by the coder 12. The application of the above criteria gives the following results:

the signals preceding the transitions in section $D_1D_2$ are not converted and are coded "support" since, up to the line passing through $D_2$, the dimensions of the flaw along Y remain less than $n_1$;

the signals preceding the transitions in section $D_2D_3$ are coded "slit", since the dimensions of the flaw are at least equal to $n_1$, but the surface of the flaw remains smaller than $n_2$ up to the line passing through $D_3$.

the signals preceding the transitions in section $D_3D_4$ are coded "hole", since, from the line passing through $D_3$, the surface of the flaw exceeds the value $n_2$.

In other words, if the flaw terminated at $D'_2$, as indicated by the hatched portion, it would be coded "support" and should not be subsequently fed to the computer. If it terminated at $D'_3$, it would be coded "support" on section $D_1D_2$ and "slit" on section $D_2D_3$.

The above-mentioned processing will therefore lead, in numerous cases, to three different codings for the same hole, or to two different codings for the same slit. In addition, the small flaws which are not to be taken into consideration are coded "support".

To obtain exploitable information from the signals written in memory 13, read-out in the memory 13 occurs in the opposite direction from the enter direction, which corresponded to the direction of analysis.

The signals other than signals S, F, T—i.e. the "leaf", "rib", "edge" and "end of line" signals—are transmitted without processing.

The signals S, F, T which arrive in the direction opposite the direction of their generation are processed in a circuit 15 in such manner that, on the one hand, the code relative to a flaw is caused to be the same over the whole extent of the flaw and, on the other hand, the signals S relative to small flaws are not transmitted.

This is achieved due to the read-out of the memory 13 effected in the direction opposite writing. If the flaw of FIG. 4 is considered, the read-out signals obtained will be, in order, T, F, S. The circuit 15 will be designed to convert a signal F present in a line X into a signal T if it is ascertained that a signal T is present in line X+1, which is the preceding read-out line, and that the position $Y_x$ of the signal F in line X is close to position $Y_{x+1}$ of the signal T in line X+1. Gradually, all the "slit" signals of the section $D_2D_3$ will be converted into "hole" signals.

Similarly, the "support" signals of section $D_1D_2$ will be converted into "hole" signals and, in all, all the transitions from $D_1$ to $D_4$ will be coded "hole", which is the desired aim.

The same process will be applied if the flaw is a slit. In this case, the "support" signals immediately following the "slit" signals (in the direction of read-out) will be converted into "slit" signals.

Finally, the "support" signals not preceded by "slit" or "hole" signals in adjacent positions Y will be eliminated since they necessarily correspond to small flaws which do not have to be taken into consideration. In this case, contrary to the general principle of transmission of the "leaf" signals, a "leaf" signal which immediately follows a "support" signal is not transmitted, so as to eliminate any trace of the flaw in the information fed to the computer.

Figure 5:
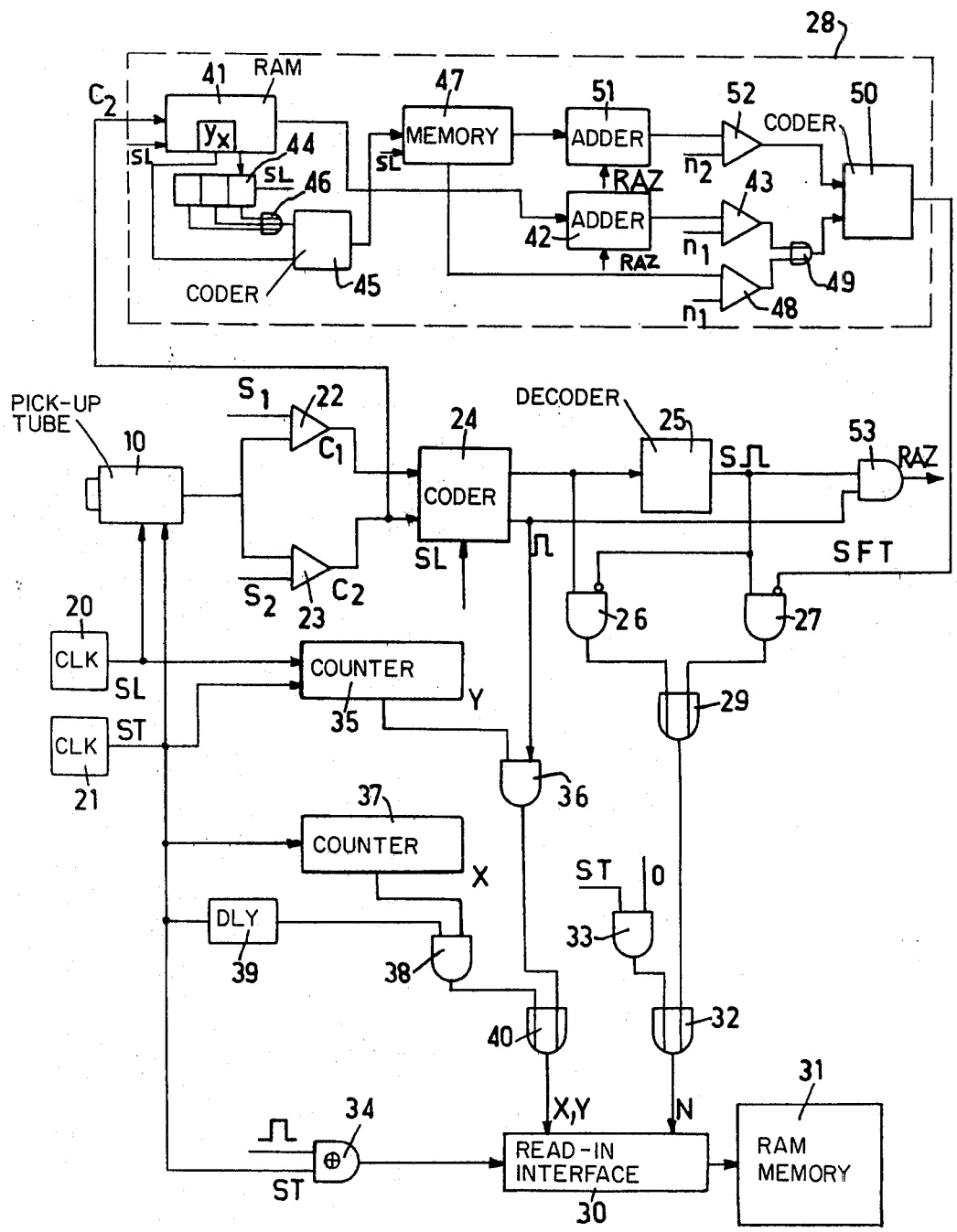
FIG. 5 shows the "input" part of the device of FIG. 3.
Figure 6:
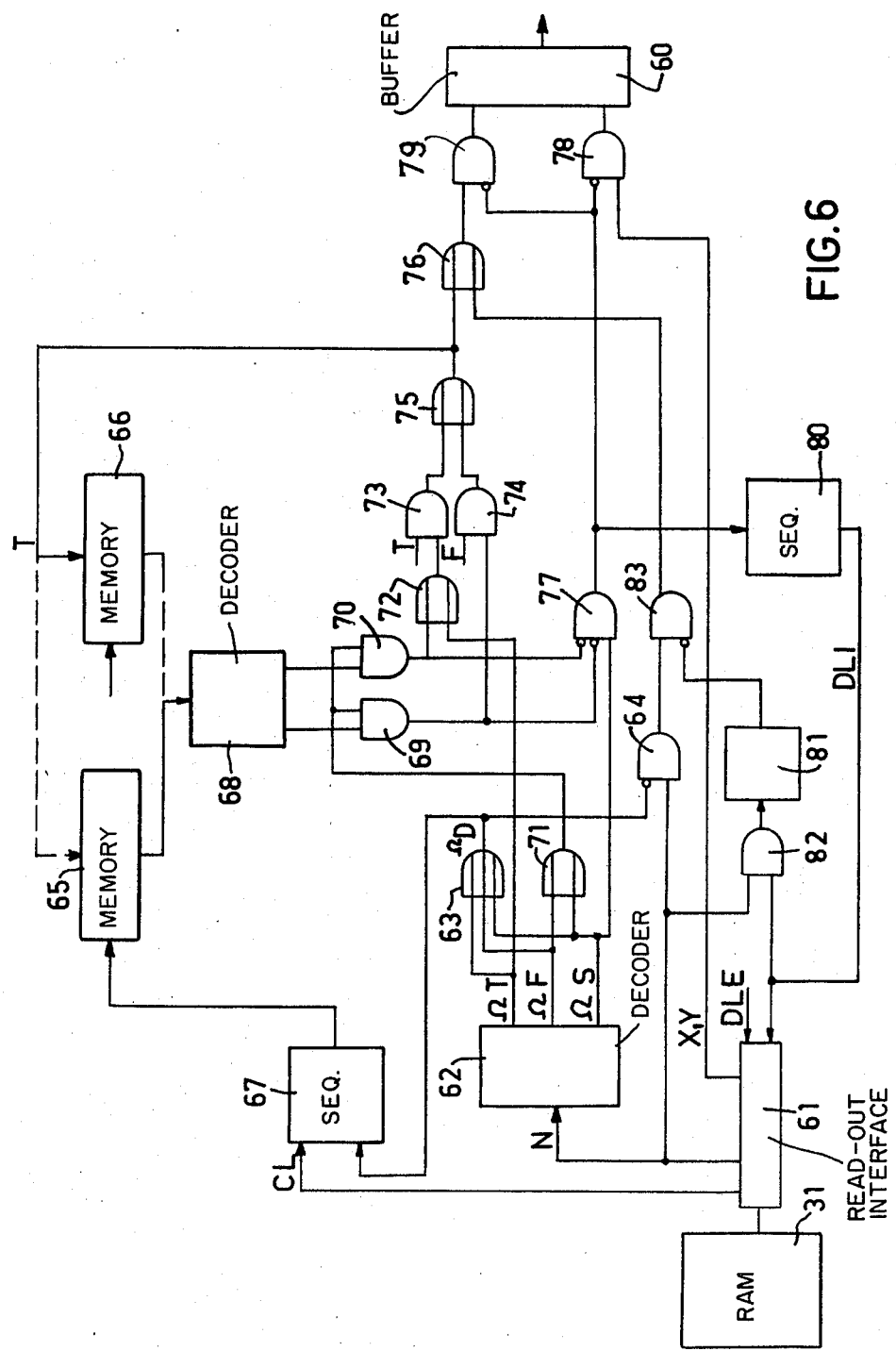
FIG. 6 shows the "output" part of the device.

The "input" part of the device of FIG. 3, namely elements 10–14 of FIG. 3, will now be described in greater detail, with reference to FIG. 5.

The pick-up tube 10 receives from a clock 20 a timing signal SL which defines the sampling frequency of the video signal, and a clock 21 supplies it with a signal ST defining the line frequency of the video signal.

Figure 2B:
FIG. 2b represents the transitions of the signal of FIG. 2a with respect to a first threshold $S_1$.
Figure 2C:
FIG. 2c represents the transitions of the same signal with respect to a second threshold $S_2$.

The video signal is compared with the thresholds $S_1$ and $S_2$ in respective comparators 22 and 23 which deliver the digital signals $C_1$ and $C_2$ shown in FIGS. 2b and 2c. These signals are applied to a coder 24 which receives the signal SL and which generates digital signals of 3 bits for each image dot, corresponding to a couple of values of $C_1$ and $C_2$.

As has been stated hereinabove, the coder delivers "rib" signals (if $C_1=0$ and $C_2=0$), "leaf" signals (if $C_1=1$ and $C_2=0$) and "support" signals (if $C_1=1$ and $C_2=1$).

The coder 24 also detects the transitions which appear in the signal $C_1$ or $C_2$ and generates a pulse ⎍ at each transition.

A special code "edge" replaces the "support" signal which immediately precedes the first negative transition of $C_2$ which is produced in a given line.

It should be noted, concerning the coder 24, that it is composed of one or more commercially available components which need simply be suitably wired in order to obtain the desired results.

The coded signals from the coder 24 are applied to a decoder 25 which delivers a pulse S⎍ only when it receives a "support" signal. The output of the coder 24 and the inverted output of the decoder 25 are applied to an AND gate 26 which therefore allows only the signals other than "support" signals to pass.

The pulses from the decoder 25 enable the transmission by the AND gate 27 of the signals from the processing circuit 28, which are thus substituted for the "support" signals delivered by the coder 24.

All the signals from gates 26 and 27, which will be called "nature" signals (N) are connected in the OR gate 29 and are applied to the read-in interface 30 of a RAM type memory 31 via an OR gate 32. The other input of the OR gate 32 is connected to an AND gate 33 which receives on the one hand the clock signal ST and, on the other hand, a zero signal, so that, with each end of line is associated a zero signal which is combined with the signals from the OR gate 29.

The writing in memory 31 of a signal from the OR gate 32 takes place only when the read-in interface 30 receives a read-in request from an exclusive OR gate 34 to which are applied the pulses ⎍ produced by the coder 34 at each transition (on $C_1$ or $C_2$). This results in that, among the signals from the gate 29, only the signals immediately preceding a transition will be entered in memory 31.

The exclusive OR gate 34 also receives the clock signal ST so as to allow the writing of the end of line signal provided by gate 33.

The read-in interface 30 further receives, in coded form, the coordinates X and Y associated with every signal from the gate 29. X defines the row of the line to which the image dot corresponding to the signal belongs, and Y defines the position of the dot in the line in question.

The coordinate Y is furnished by a counter 35 which receives the clock signals SL and ST, and whose output is applied to an AND gate 36 receiving on the other hand the transition pulses ⎍ from the coder 24.

The coordinate X is furnished by a counter 37 which receives the clock signal ST. The output of the counter 37 is connected to an AND gate 38 also connected to a delay line 39, and whose output is connected to the OR gate 40 also connected to the output of the AND gate 36.

Consequently, the data Y are entered only for the dots preceding a transition, this establishing the correspondence between the stored data Y and the coded signals from the gate 29 which are entered in the memory 31. As to data X, they are entered at the beginning of each line.

The processing circuit will now be described in greater detail.

A RAM type memory 41 receives the signal $C_2$ from the comparator 23 as well as the clock signal SL. The signals which are entered in the memory 41 therefore each correspond to an image dot. These signals are in state "1" when the corresponding dots belong to the support. The capacity of the memory 41 is just sufficient to contain the signals $C_2$ of a line. This capacity is therefore 1728×1 bit since one line comprises 1728 dots. This results in that the read-in of the signals of a line X causes the signals of preceding line X−1 to be erased.

The output of the memory 41 is connected to an adder 42 which delivers a signal representative of the number of consecutive "1"s which are fed thereto by the memory 41. The adder 42 is reset to zero when it receives a pule RAZ from an AND gate 53 receiving the pulses ⎍ from the coder 24 and the pulses S⎍ from the decoder 25. The resetting to zero is therefore effected upon the transition which indicates the end of the flaw in a line (for example points $D_2,D_3$ in FIG. 4).

The signal from the adder 42 is therefore indicative of the dimensions along Y of the corresponding flaw. This signal is applied to a threshold device 43 whose output is in state "1" if the input signal is greater than a value $n_1$ equal to 12 in the present example.

To determine the dimensions of the flaw along X, the number of "1"s which follow in successive lines must be counted. To this end, the content of the memory 41 for a dot Y of a line X must be compared with the values obtained for points $Y-1$, Y and $Y+1$ of the preceding line $X-1$. This is achieved due to a 3-stage shift register 44 in which is stored the value $Y+1$ of line $X-1$ at the same time as the value Y of line X is entered in memory 41. The read-in of the value $Y+1$ in the register 44 causes a shifting by one step, so that the register permanently contains the values $Y-1$, Y and $Y+1$ of line $X-1$. The read-in in memory 41 and transfer in register 44 are effected during the first half of a period of signal SL.

During the second half, the value $Y_x$ which has just been stored in the memory 41 and the values $Y-1$, Y and $Y+1$ of line $X-1$ contained in register 44 are read. A coder 45 receives, on the one hand, the value $Y_x$ and on the other hand the output signal of an OR gate 46 connected to the three stages of the register 44. The coder 45 supplies a RAM memory 47 of the same type as memory 41, but with a capacity of $1728 \times 3$ bits.

The coder 45 may supply the memory 47 with three different signals according to the signals which are applied thereto.

If the value $Y_x$ read in the memory 41 is "0", the coder 45 delivers a signal which controls the read-in of a "0" in the memory 47.

If the value $Y_x$ is "1" and the values read in the shift register 44 are all equal to "0", the coder 45 delivers a signal which controls the read-in of a "1" in memory 47. This means that a flaw begins.

Finally, if the value $Y_x$ is "1" and at least one of the values read in the register 44 is equal to "1", the storing of the flaw has already started in the preceding line. The coder 45 then delivers a signal which controls the incrementation of the corresponding stage of memory 47. The memory 47 thus furnishes the dimensions of the flaw along X or along a slope of 45° at the most, the value $Y_x$ being compared not only with the value Y of line $X-1$, but also with the adjacent values $Y-1$ and $Y+1$.

The value read in the memory 47 is applied to a threshold device 48 similar to the device 43, which delivers a pulse when the input signal exceeds the above-mentioned value $n_1$—therefore when the dimensions of the flaw along X exceed 3 mm.

The outputs of the threshold devices 43 and 48 are connected in an OR gate 49 whose output is connected to a coder 50 delivering 3 bit words.

On the other hand, the values contained in the memory 47 are added in an adder 51 similar to adder 42, which is also reset to zero by the pulses RAZ. The adder 51 effects the addition along Y of the values contained in the memory 47, which are sums along X. The output value of the adder 51 is therefore indicative of the surface of the flaw.

This value is compared with the above-mentioned value $n_2$, corresponding to 4 mm², in a threshold device 52 which delivers a pulse to the coder 50 when the input signal is greater than $n_2$.

Three cases may therefore be encountered.

If the output of the gate 49 is in state "0", the flaw has dimensions smaller than $n_1$ and may not be taken into consideration. The coder 50 delivers a signal S (support).

If the gate 49 delivers a pulse, but the output of the device 52 is in state "0", the flaw has dimensions greater than $n_1$, but a surface smaller than $n_2$. This is a slit and the coder 50 delivers a signal F.

Finally, if the output of the device 52 and that of the gate 49 are in state "1", the flaw has dimensions greater than $n_1$ and a surface greater than $n_2$: this is a hole, for which the coder 50 delivers a signal T.

It should, of course, be noted that the words delivered by the coder 50 are chosen to be different from those which may be provided by the gate 26.

As has been stated hereinabove, the signals from the coder 50, which constitutes the output of the circuit 28, are applied to the gate 27 which applies them to the gate 29 when it receives a pulse S from the decoder 25. The signals S, F, T having replaced the "support" signals are entered in the memory 31 via the gates 29 and 32.

The codes which may be associated with a given position Y on the line X are therefore: leaf-rib-S (support)-F (slit)-T (hole)-edge-end of line.

The memory 31 has a capacity which allows a complete image of the leaf to be stored, it being understood that only the signals preceding transitions are recorded, with their position Y, and the position X at the beginning of each line. A capacity of 32 K words is sufficient in the present example.

The "output" part of the device will now be described, which processes the information recorded in the memory 31 and applies the same to a buffer 60 acting as intermediary with the computer.

Read-out of the memory 31 is effected as the buffer 60 empties, as each read-out of the buffer 60 triggers off a read-out request DLE applied to the read-out interface 61 of the memory 31.

The memory 31 is read out in the order opposite the read-in order, i.e. the order of read-out of the lines is $X+1$, X, $X-1$, etc.

The "nature" signals N read in the memory 31 are applied to a decoder 62 having three outputs and which delivers a pulse ⎍_S on one of the outputs if the input signal is a "support" signal S, a pulse ⎍_F on another output if the input signal is "slit" and a pulse ⎍_T if the applied signal is "hole".

The pulses ⎍_S, ⎍_F and ⎍_T are applied to an OR gate 63 whose output is connected, once inverted, to an AND gate 64 receiving on the other hand the signals N. The gate 64 consequently passes all the signals N with the exception of signals S, F and T corresponding to flaws.

To perform the above-described processing of signals S, F, T, consisting in rendering homogeneous the coding of a flaw and in eliminating the "support" codes pertaining to unsignificant flaws, each signal S or F occupying position Y in a line X is compared with the signals the positions of which are between positions $Y-n_4$ and $Y+n_4$ of line $X+1$, which is read before line X. If a signal T is found, the signals S or F are converted into signals T, and if a signal F is found, the signals S are converted into signals F. In the present example, $n_4$ is chosen to be equal to 3.

To perform this comparison, two alternately operating RAM type memories 65 and 66 are used, the read-out of one being effected during the writing in the other. In FIG. 5, the memory 65 is the "preceding" memory which is read, and the memory 66 is the "present" memory in which data are entered.

The operation of the memories 65 and 66 is controlled by a sequencer 67, constituted by a PROM element, which receives the pulses ⌐⌐$_D$ from gate 63, as well as line change pulses CL from the read-out interface 61. Upon reception of a pulse CL, the sequencer 67 triggers alternation of the memories 65 and 66.

The outputs of the memories 65 and 66 are connected to a decoder 68 having two outputs respectively connected to AND gates 69 and 70. The decoder delivers a pulse to gate 69 when it receives a signal F and to gate 70 when it receives a signal T. The other inputs of the gates 69 and 70 are connected to the output of an OR gate 71 which receives the pulses ⌐⌐$_F$ and ⌐⌐$_S$ from the decoder 62.

The output ⌐⌐$_T$ of the decoder 62 and the output of the gate 70 are connected to an OR gate 72 which, when it is in state "1", enables the transmission of the signal T by an AND gate 73. An AND gate 74 transmits the signal F when the output of the gate 69 is in state "1".

The outputs of gates 73 and 74 are connected to an OR gate 75 whose output is connected to the memories 65 and 66 for read-in purposes.

In view of the foregoing, only the signals F and T are stored in the "present" memory, namely memory 66 in the case of the drawing.

On the other hand, it is clear that the signals T read in memory 31 are transmitted without modification. The signals T delivered at the output of the gate 75 are stored in memory 66. The read-in of a signal T in the "present" memory triggers off, at the same time, the return to zero of the corresponding stage in the "preceding" memory.

If the signal which is applied to the decoder 62 is a signal S or F, the sequencer 67 triggers off readout in the "preceding" memory 65 of compartments Y−3 to Y+3, Y being the position of the incoming signal. If in one of these stages a signal F or T has been entered, the decoder 68 produces a pulse on one of its outputs which enables the transmission of the output signal of the gate 71, either by gate 69, or by gate 70. If gate 69 is enabled, a signal F is obtained at the output of gate 75, and if it is gate 70, a signal T is obtained.

The signals F or T delivered by the gate 75 are applied to the OR gate 76 together with the signals from the AND gate 64 and passed by the AND gate 83 (described hereinafter), which are all signals other than the codes S, F, T.

On the other hand, the production of a pulse by one of the gates 69 and 70 inhibits the AND gate 77 which receives the pulses ⌐⌐$_S$ from the decoder 62. Consequently, the gate 77 passes only the pulses ⌐⌐$_S$ corresponding to negligible flaws, since only the latter can result in signals S not followed (in the direction of the analysis) by signals F or T. The production of a pulse by the gate 77 inhibits the AND gate 78 which normally provides the positions X or Y read in the memory 31, so that the positions X or Y of the signals S corresponding to negligible flaws are not transmitted, in accordance with one of the desired purposes. Similarly, the pulses from the gate 77 inhibit the AND gate 79 connected to the output of the gate 76.

The output of the gate 77 is also connected to a sequencer 80 constituted by a PROM element, which applies a read-out request DLI to the read-out interface 61 when it receives a pulse from gate 77. This request DLI triggers off the read-out of the following signal—i.e. the preceding signal in the direction of the analysis. If the sequencer 80 identifies the following signal as being a "leaf" signal, which therefore corresponds to the beginning of an unsignificant flaw, this signal is not passed and the sequencer 80 delivers a new request DLI, after which a signal is transmitted and read-in is again controlled by the requests DLE from the buffer 60. If the following signal is not a "leaf" signal, the sequencer 80 becomes inoperative and the following read-out request is made from buffer 60.

This is obtained by means of a decoder 81 which receives the signals N from an AND gate 82 enabled by the request DLI produced by the sequencer 80. If the decoder 81 receives a "leaf" signal, it delivers a pulse which inhibits the AND gate 83, preventing the transmission of the "leaf" signal towards buffer 60.

The preceding description relates to the application of the invention to the cut-out of cigar wrappers from tobacco leaves. However, it is obvious that the invention is not limited to this application, but is applicable in all cases where the shape of a product which may comprise holes is to be analysed. The criteria used for analysis of the holes may vary depending on the case. For example, it may suffice to apply one single dimensional criterion, by distinguishing only between negligible flaw and flaw to be taken into consideration and dropping the distinction between hole and slit. A single code "flaw" would then replace the codes "hole" and "slit".

Similarly, the distinction between leaf and rib is particular to the application described and will not be applied elsewhere.

If such distinctions are not necessary, the processing may be carried out with circuits which are notably simplified with respect to the circuits described hereinabove. The modifications to be made in each case, which may simply consist in eliminating elements, are perfectly within the purview of one skilled in the art.

What is claimed is:

1. A process for deriving digital information indicative of the outer contour of a leaf-like article and of the holes which it may comprise, said holes having to be taken into consideration for the use of the article when their dimensions exceed a determined threshold, from a sampled analog video signal composed of image lines and representing the image of the article placed on a support, said process comprising the steps of comparing the video signal, for each image dot or sample, with a threshold and coding the dot "1" or "0" according to the result of the comparison; detecting the transitions in the digital signal thus obtained; coding this digital signal as a "leaf" signal or word when the signal is in state "0" (or "1") and as a "support" word when the signal is in state "1" (or "0") and when it relates to a hole; comparing with the above-mentioned threshold, expressed by a number $n_1$ of image dots, the number n of dots coded "1" (or "0") which follow one another, firstly in a line X (direction Y), then in consecutive lines X, X+1, etc. (direction X); converting the "support" signals if n÷$n_1$, into "flaw" signals and transmitting them unchanged if n<$n_1$; storing solely the signals preceding a transition, together with corresponding position data Y, by writing them line by line as said lines appear; reading the stored information in an order opposite the order of writing, whereby line X+1 is read before line X; transmitting the signals other than the "support" signals unaltered, and processing the "support" signals as follows: if a "support" signal of a line X is located in the vicinity of a "flaw" signal present in previously read line X+1, it is converted into a "flaw" signal, and if this is not the case, it is not transmitted.

2. An apparatus for delivering digital information indicative of the outer contour of a leaf-like article and and of holes which it may include, said apparatus comprising: means for delivering a sampled analog video signal in the form of successive image lines, a comparator for comparing the video signal with a threshold and delivers a digital signal according to said comparison, a coder connected to receive an input signal from the comparator for delivering a pulse when transition occurs in the input signal and for delivering a digital signal or words according to the value of the input signal and the transitions, a processing circuit for receiving the digital signal from the comparator and counting the number of consecutive "1"s (or "0"s) in one line X and in successive lines X, X+1, etc. and delivering "support" or "flaw" words depending on whether said number is lower than or higher than a value $n_1$, a switching circuit connected to the coder and to the processing circuit for substituting the words from the processing circuit for the corresponding words from the coder, a memory of which the directions of read-in and read-out are opposite and in which the signals from the switching circuit are entered together with their positions Y under the control of the transition pulses from the coder, an output circuit for receiving the stored "support" signals and converting a "support" signal located in line X in the vicinity of at least one "flaw" signal located in the line X+1 into a "flaw" signal and without passing the "flaw" signals from said circuit and the other signals from said memory.

3. The apparatus of claim 2, wherein the output circuit comprises two memories arranged for alternate operation in one of which are entered the signals of line X at the same time as those of X+1 are read-out in the other memory, and means for comparing the state of the signal in the position Y of line X with the states of the signals in positions $Y-n_4$ to $Y+n_4$ of line X+1.

4. The apparatus of claim 2, wherein the read-out of the memory is controlled from the buffer and a sequencer is provided for controlling the read-out of a word in the memory when the preceding word is a "support" signal which has not been transmitted, and a circuit for preventing the transmission of this word if it is a "leaf" signal.

5. The apparatus of claim 2, wherein the processing circuit comprises a first memory connected to the comparator, means for comparing the state of the signal in the position Y of the line X with the states of the signals $Y-1$, Y and $Y+1$ of line $X-1$, a second memory incremented each time the above-mentioned signal is in state "1" (or "0") at the same time as at least one of said signals of the line $X-1$, an adder connected to said first memory, threshold devices connected respectively to the adder and to the second memory to compare their contents with value $n_1$, and a coder connected to said threshold devices.

6. The apparatus of claim 5, wherein a three-stage shift register is associated with the first memory, the signal $Y+1$ of line $X-1$ being transferred from said memory in the register at the same time as the signal Y of line X is entered in the memory.

7. The apparatus of claim 5, wherein a second adder is added to the second memory and a threshold device compares the contents of the second adder with a value $n_2$, this device being connected to said coder.

* * * * *